United States Patent [19]

Antos

[11] 3,962,035

[45] June 8, 1976

[54] HYDROCARBON CONVERSION PROCESS

[75] Inventor: George Antos, Arlington Heights, Ill.

[73] Assignee: Universal Oil Products Company, Des Plaines, Ill.

[22] Filed: June 24, 1974

[21] Appl. No.: 482,122

[52] U.S. Cl. .............................. 195/27; 260/676 R; 210/15
[51] Int. Cl.² .......................................... C07C 9/00
[58] Field of Search ..................... 195/28 R, 33, 29; 210/2, 11, 15, 16; 71/9; 260/683.9, 676 R, 682, 526

[56] References Cited
UNITED STATES PATENTS

| | | | |
|---|---|---|---|
| 3,383,309 | 5/1968 | Chandler | 210/11 |
| 3,476,803 | 11/1969 | Pine | 260/676 R |

OTHER PUBLICATIONS

March "Advanced Organic Chemistry: Reactions, Mechanisms and Structure" McGraw–Hill 1968 pp. 435–436 and 477–480.

*Primary Examiner*—A. Louis Monacell
*Assistant Examiner*—R. B. Penland
*Attorney, Agent, or Firm*—James R. Hoatson, Jr.; Raymond H. Nelson; William H. Page, II

[57] ABSTRACT

A process for the production of hydrocarbonaceous materials which comprises reacting waste materials with a microorganism to produce organic products and treating the resultant organic products with a catalyst comprising a decarboxylation catalyst is disclosed.

7 Claims, No Drawings

HYDROCARBON CONVERSION PROCESS

This invention relates to a process for the production of hydrocarbon materials. More specifically, this invention relates to a process for the preparation of hyrocarbon materials which comprises reacting waste materials with a microorganism to produce organic products and treating the organic products with a catalyst comprising a decarboxylation catalyst.

It has been shown in the prior art that waste materials may be utilized to prepare hydrocarbonaceous materials in a reaction process in which extremely high temperatures and pressures are utilized. It is also known in the art that waste materials may be treated with microorganisms as is common in various sewage and sewage sludge plants. It is also known in the prior art that carboxylic acids may be decarboxylated to the corresponding saturated or unsaturated hydrocarbon by use of pressure, temperature and a suitable decarboxylation catalyst.

In contradistinction to the prior art it has now been discovered that a process for the preparation of hydrocarbon materials may be performed which comprises reacting waste materials with a microorganism to produce organic products, particularly carboxylic acids, and treating the resultant organic products with a catalyst comprising a decarboxylation catalyst to produce the hydrocarbon materials. The utilization of the present invention will allow the manufacturer a more inexpensive method for the production of the hydrocarbon materials as a result of the utilization of lower temperatures and pressures compared with those currently used in pyrolysis techniques. The manufacturer will also have the benefit of performing the preparation of the hydrocarbon materials in either an aerobic or an anaerobic atmosphere, in which the organic products produced from the reaction of the waste materials and the microorganisms are controlled to a greater degree of precision. The utilization of the above cited invention will also allow the manufacturer of the hydrocarbon material to possess a greater control over the type and length of chain of the hydrocarbon materials prepared as a result of the various microorganisms and decarboxylation catalysts which may be employed. The utilization of the above set forth invention will also allow the manufacturer a source of sulfur-free hydrocarbon materials which may be easily converted into gasoline or heating oil. Nationally, the utilization of the above set forth invention will allow for a greater United States independence of energy resources in compliance with the national effort to become energy independent by the year 1980.

The desired products of the process of this invention, namely, hydrocarbon materials are utilized in the chemical industry in many ways. For example, hydrocarbon materials may be refined or used as gasoline or heating oil; in the manufacture of candles; as alkylating agents; as solvents for other chemicals such as the use isooctane(2,2,4-trimethylpentane); or as starting materials for the production of other chemicals and products.

It is therefore an object of this invention to provide a process for the preparation of hydrocarbon materials.

A further object of this invention is to provide a process for the preparation of hydrocarbon materials utilizing certain microorganisms and catalytic compositions of matter which will permit the recovery of the desired hydrocarbon materials in a more expedient manner.

In one aspect an embodiment of this invention resides in a process for the preparation of hydrocarbon materials which comprises reacting waste materials with a microorganism at reaction conditions in an aerobic or anaerobic atmosphere to produce organic products, treating the resultant organic products with a catalyst comprising a decarboxylation catalyst at treatment conditions to produce hydrocarbon materials, and recovering the resultant hydrocarbon materials.

A specific embodiment of this invention resides in a process for preparing hydrocarbon materials having a chain length of from about 1 to about 15 carbon atoms whereby the chain length is saturated, which comprises reacting dewatered human waste with a microorganism from the genus of Butyribacterium to product various carboxylic acids at a reaction temperature of from about 25° to 100°C in an anaerobic atmosphere (absence of free oxygen) and treating the resultant carboxylic acid products with a catalyst comprising phosphoric acid at a treatment temperature of from about 50°C to about 200°C and a pressure of 1 atmosphere, and recovering the resultant hydrocarbon materials having a chain length from between 1 to about 15 carbon atoms, said hydrocarbon materials being predominantly saturated compounds.

A second specific embodiment of this invention resides in a process for preparing a hydrocarbon material having from between 1 to about 15 carbon atoms which comprises reacting dewatered animal waste with a microorganism from the genus of Propionibacterium at a temperature of 50°C in an aerobic (free oxygen present) atmosphere to produce carboxylic acids possessing carbon atoms from about 1 to about 15 carbon atoms in length and treating said produced carboxylic acids with a decarboxylation catalyst comprising sodium hydroxide at a temperature of 250°C and a pressure of 50 atmospheres afforded by the introduction of a substantially inert gas such as nitrogen and recovering the resultant hydrocarbon material having from about 1 to about 15 carbon atoms, said hydrocarbon material being predominantly saturated.

Other objects and embodiments will be found in the following further detailed description of the present invention.

As hereinbefore set forth, the present invention is concerned with a process for preparing hydrocarbon materials which comprises reacting waste materials with a microorganism to produce organic products, predominantly carboxylic acids, and treating the resultant organic products with a catalyst comprising a decarboxylation catalyst. The reaction of the waste products with the microorganism is effected under reaction conditions which include a temperature of from about 25°C to about 250°C and in an atmosphere which is either aerobic or anaerobic in nature. The treatment of the resultant organic products with a decarboxylation catalyst is effected at treatment conditions which include a temperature of from about 25°C to about 500°C and a pressure from about 1 atmosphere to about 100 atmospheres. When superatmospheric pressures are employed, said pressure is afforded by the introduction of a substantially inert gas such as nitrogen or helium to the reaction zone.

Examples of suitable waste material which may be utilized as one of the starting materials of the present invention will include solid human waste, solid animal waste, rubbish, "household" garbage, industrial garbage, industrial wastes and unwanted by-products, sewage, sewage sludge, etc.

Suitable examples of microorganisms which may be utilized in the process of the present invention include bacteria, yeasts, molds and protozoa. The types of bacteria which may be utilized include genera such as Propionibacterium, Butyribacterium, Microbacterium, Corynebacterium, Listeria, Lactobacillus, Brevibacterium, Kurthia, Clostridium, Micrococcos, Staphylococcus, Gaffkya, Sarcina, Diplococcus, Streptococcus, Leuconostoc, Neisseria, Veillonella, Azotobacter, Rhizobium, Alcaligenes, Achromobacter, Flavobacterium, Escherichia, Aerobacter, Klebsiella, Paracolobactrum, Erwinia, Proteus, Salmonella, Shigella, Pasteurella, Brucella, Haemophilus, Bacteroides, Fusobacterium, etc.

Specific examples of yeasts contemplated within the scope of this invention would include the genera Candida, Cryptococcus, Nematospora, Lipomyces, Saccharomyces, Schizosaccharomyces, etc. Suitable examples of molds would include the genera Cryptococcus, Fusarium, Penicillium, Neurospora, Rhizopus, Sapromyces, etc. Suitable examples of protozoa would include the genera Amoeba, Euglena, Paramecium, Badhamia, etc.

Suitable examples of carboxylic acids which may be produced from the reaction of the waste material with the microorganism will include all carboxylic acids and polycarboxylic acids possessing of from about 1 carbon atom to about 20 carbon atoms or more. Specific examples of said carboxylic acids would include acetic acid, propionic acid, butyric acid, isobutyric acid, n-valeric acid, trimethylacetic acid, caproic acid, n-heptylic acid, caprylic acid, pelargonic acid, decanoic acid, undecanoic acid, dodecanoic acid, tridecanoic, tetradecanoic acid, pentadecanoic acid, heptadecanoic acid, octadecanoic acid, nonadecanoic acid, eicodecanoic acid.

Suitable examples of catalyst which may be utilized in the process of the present invention include all decarboxylation catalysts such as zinc, hydrogen sulfide, aluminum, chromium, aluminum oxide, chromium oxide, sodium carbonate, calcium carbonate, copper sulfate, platinum, iridium, ruthenium, palladium, osmium, rhodium, zinc oxide, silica, sulfurized naphthenes, barium carbonate, sodium hydroxide, iron, phosphoric acid, barium fluoride, etc. The aforementioned catalysts may be utilized in any suitable form such as a powder, granules or preformed shapes. It is also contemplated within the scope of the present invention that the decarboxylation catalyst may be dispersed or coated on a support material, which may be inert or may itself possess catalytic properties such as alumina, silica, titania, pumice, etc.

The process of the present invention may be effected in the presence of any one of several mediums. The microbial treatment of the waste material may be effected in an aqueous medium and the decarboxylation may be effected in the presence of an aqueous medium or any inert material such as n-pentane, n-hexane, 2,2,4-trimethylpentane (isooctane), benzene, toluene, xylene, etc. It is understood that the aforementioned waste materials, microorganisms, organic acids, decarboxylation catalysts and process medium are only representative of the class of compounds which may be employed, and that the present invention is not necessarily limited thereto.

It is contemplated within the scope of this invention that the process for the preparation of the hydrocarbon materials may be performed in a continuous manner of operation. When such a type of operation is employed the reactants comprising the waste material and the microorganisms are charged to a reaction vessel maintained at predetermined conditions of temperature and possessing either an anaerobic (free oxygen absent) or an aerobic (free oxygen present) atmosphere. After completion of the desired residence time, the organic compounds produced, namely carboxylic acids, are continuously withdrawn and subsequently charged to a second treatment zone wherein they are treated with a catalyst comprising a decarboxylation catalyst. The organic products are maintained in the treatment zone for a period of time of about 0.5 to about 25 hours or more at predetermined conditions of temperature and pressure. The hydrocarbon material formed in the treatment zone is withdrawn as the reactor effluent while any untreated organic products are recycled to the treatment zone and any unreacted microorganisms or waste material are recovered and recycled to the first reaction zone. It is also contemplated that the above set forth invention may be practiced in a batch type operation although the continuous method of operation is the desirable mode of operation.

Inasmuch as the catalytic composition of matter may be solid in nature, various types of continuous operation may be utilized. One such type comprises the fixed bed method in which the catalyst is disposed as a fixed bed in the treatment zone and the organic products are passed over said fixed bed in either an upward or downward flow or alternatively, fluidized beds may also be employed.

Another feature of this invention is the inclusion of separation techniques to aid in optimum process operations. The products of microbial treatment may be subjected to separation procedures in order to separate the carboxylic acids from the other organic products prior to catalytic decarboxyaltion. Examples of these separation techniques may include solvent extraction, precipitation, complexation, acid-base reaction, etc.

The following examples are given to illustrate the process of the present invention which, however, are not intended to limit the generally broad scope of the present invention in strict accordance therewith.

EXAMPLE I

In this example 0.5 grams of dewatered human waste and 0.05 grams of a microorganism consisting of *Butyribacterium rettgeri* are charged to a reaction zone maintained under an anaerobic atmosphere at a temperature of 27°C. The product is recovered from the reaction zone after a period of time comprising 2 hours and divided into two parts. The first part is analyzed by means of gel permeation chromatography and found to contain predominantly carboxylic acids possessing between 1 carbon atoms and 21 carbon atoms. The second part of the sample is charged to a treatment zone containing a decarboxylation catalyst comprising phosphoric acid, said treatment zone being maintained at a temperature of 100°C and a pressure of 1 atmosphere. The second part of the sample is treated for a residence time comprising 2 hours in the treatment zone at which time the resultant product is removed and analyzed by means of gas-liquid chromatography instrumentation, said analysis disclosing the resultant product to be a predominantly saturated hydrocarbon material possessing from 1 carbon atom to about 20 carbon atoms. The treated product was also analyzed for sulfur content, said analysis disclosing the reaction product to be sulfur-free.

EXAMPLE II

In this example 0.75 grams of dewatered animal waste and 0.03 grams of a microorganism consisting of *Proprionibacterium freudenreichii* are charged to a reaction zone maintained under an aerobic atmosphere at a temperature of 50°C. The product is recovered from the reaction zone after a period of time comprising 4 hours and divided into two parts. The fist part is analyzed by means of gel permeation chromatography and found to contain predominantly carboxylic acids possessing between 1 carbon atom and 21 carbon atoms. The second part of this sample is charged to a treatment zone containing a decarboxylation catalyst comprising sodium hydroxide, said treatment zone being maintained at a temperature of 250°C and a pressure of 50 atmospheres as afforded by the introduction of substantially inert nitrogen. The second part of this example is treated for a residence time comprising 3 hours in the treatment zone, at which time the resultant product is removed and analyzed by means of gas-liquid chromatography instrumentation, said analysis disclosing the resultant product to be a predominantly saturated hydrocarbon material possessing from 1 carbon atom to 15 carbon atoms. The resultant product was also analyzed for sulfur content, said analysis disclosing the resultant product to be sulfur-free.

EXAMPLE III

In this example 0.44 grams of sewage sludge and 0.07 grams of *Acetobacter aceti* are charged to a reaction zone maintained under an aerobic atmosphere at a temperature of 75°C. The reaction product is recovered from the reaction zone after a period of time comprising 4 hours of residence and divided into two parts. The first part is analyzed by means of gel permeation chromatography and found to contain predominantly carboxylic acids possessing between 1 and 21 carbon atoms. The second part of the sample is charged to a treatment zone containing a decarboxylation catalyst comprising barium fluoride, said treatment being maintained at a temperature of 500°C and a pressure of 100 atmospheres as afforded by the introduction of substantially inert nitrogen. The second part of the sample is treated for a residence time comprising 2 hours in the treatment zone at which time the resultant product is removed and analyzed by means of gas-liquid chromatography instrumentation, said analysis disclosing the resultant product to be a predominantly saturated hydrocarbon material possessing from 1 carbon atom to 15 carbon atoms. The resultant product is also analyzed for sulfur content, said analysis disclosing the product to be sulfur-free.

The above set forth experiment is twice repeated using zinc oxide and secondly ruthenium as a decarboxylation catalyst in the place of the barium fluoride, said experiment concluding in the same result, namely that the reaction product was a predominantly saturated hydrocarbon material possessing from 1 carbon atom to about 15 carbon atoms. The resultant reaction product is also found to be sulfur-free when zinc oxide and ruthenium are utilized as the decarboxylation catalysts.

I claim as my invention:

1. A process for converting waste material selected from the group consisting of animal waste, human waste and sewage sludge to prepare a saturated hydrocarbon fraction consisting essentially of gasoline which comprises:

a. reacting said waste material with a microorganism selected from the group consisting of *Butyribacterium rettgeri*, *Proprionibacterium freudenreichii* and *Acetobacter aceti* at a temperature of from 25°C. to 75°C. in an aerobic or anaerobic atmosphere to produce alkanoic acids containing up to 10 carbon atoms;

b. subjecting said alkanoic acids to catalytic decarboxylation to form said saturated hydrocarbon fraction at catalytic decarboxylation conditions; and c. recovering said saturated hydrocarbon fracton.

2. The process of claim 1 further characterized in that the catalytic decarboxylation conditions include a temperature of from 15°C. to 500°C. and a pressure of up to and including 100 atmospheres.

3. The process of claim 1 further characterized in that the decarboxylation catalyst is phosphoric acid.

4. The process of claim 1 further characterized in that the decarboxylation catalyst is sodium hydroxide.

5. The process of claim 1 further characterized in that the decarboxylation catalyst is barium fluoride.

6. The process of claim 1 further characrerized in that the decarboxylation catalyst is zinc oxide.

7. The process of claim 1 further characterized in that the decarboxylation catalyst is ruthenium.

* * * * *